United States Patent

McQuire et al.

[11] Patent Number: 6,043,365
[45] Date of Patent: Mar. 28, 2000

[54] PREPARATION OF 2-AMINO-7-(1-SUBSTITUTED-2-HYDROXYETHYL)-3, 5-DIHYDROPYRROLO[3,2-D]PYRIMIDIN-4-ONES

[75] Inventors: Leslie W. McQuire, Morristown; Benjamin B. Mugrage, Basking Ridge; Mahavir Prashad, Montville; John H. van Duzer, Asbury, all of N.J.

[73] Assignee: Novartis AG, Basel, Switzerland

[21] Appl. No.: 09/086,043

[22] Filed: May 28, 1998

Related U.S. Application Data

[60] Provisional application No. 60/048,018, May 29, 1997.

[51] Int. Cl.$^7$ .................................................. C07D 487/04
[52] U.S. Cl. ............................................. 544/280; 544/238
[58] Field of Search ........................................ 544/280, 238

[56] References Cited

U.S. PATENT DOCUMENTS

| | | | |
|---|---|---|---|
| 4,923,872 | 5/1990 | Kostlan et al. | 514/258 |
| 5,189,039 | 2/1993 | Niwas et al. | 514/258 |
| 5,565,463 | 10/1996 | Secrist, III et al. | 514/265 |
| 5,726,311 | 3/1998 | Niwas et al. | 544/232 |

FOREIGN PATENT DOCUMENTS

| | | |
|---|---|---|
| WO 91/06548 | 5/1991 | WIPO . |
| WO 93/21187 | 10/1993 | WIPO . |

OTHER PUBLICATIONS

Ealick, et al., Proc. Natl. Acad. Sci., vol. 88, pp. 11540–11544 (1991).

Erion, et al., J. Med. Chem., vol. 36, pp. 3771–3783 (1993).

Lim, et al., J. Org. Chem., vol. 44, No. 22, pp. 3826–3829 (1979).

Lim et al., J. Org. Chem., vol. 48, pp. 780–788 (1983).

*Primary Examiner*—Emily Bernhardt
*Attorney, Agent, or Firm*—Norbert Gruenfeld

[57] ABSTRACT

The compounds of formula I

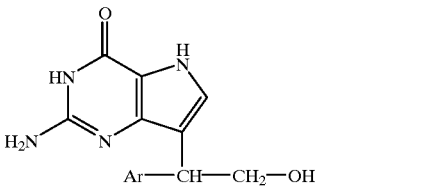

wherein Ar represents biaryl, carbocyclic or heterocyclic aryl, are prepared, as substantially pure enantiomers, by (a) condensing a compound of the formula

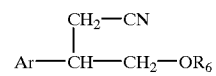

as a substantially pure enantiomer, wherein Ar has meaning as defined above and $R_6$ is on O-protecting group with a lower alkyl ester of formic acid;

(b) then condensing the compound so obtained with a compound of the formula

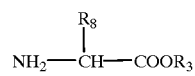

wherein $R_8$ is hydrogen or $COOR_3$ and $R_3$ is lower alkyl;

(c) then cyclizing the compound so obtained to a compound of the formula

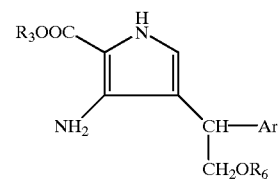

as a substantially pure enantiomer;

(d) and then condensing the compound so obtained
   (1) with a carbocyclic aroyl isothiocyanate and treatment of the product so obtained with an alkyl halide followed by anhydrous ammonia; or
   (2) with cyanamide in acid, optionally followed by treatment with a base.

14 Claims, No Drawings

PREPARATION OF 2-AMINO-7-(1-SUBSTITUTED-2-HYDROXYETHYL)-3,5-DIHYDROPYRROLO[3,2-D]PYRIMIDIN-4-ONES

CROSS-REFERENCE TO RELATED APPLICATIONS

This application claims the benefit of provisional application Ser. No. 60/048,018 filed May 29, 1997.

BACKGROUND AND SUMMARY OF THE INVENTION

The invention relates to the 9-deazaguanine derivatives, namely 2-amino-7-(1-substituted-2-hydroxyethyl)-3,5-dihydro-pyrrolo[3,2-d] pyrimidin-4-ones as defined herein which are particularly potent purine nucleoside phosphorylase (PNP) inhibitors, methods for preparation thereof, pharmaceutical compositions comprising said compounds, and a method of inhibiting purine nucleoside phosphorylase and of treating conditions in mammals which are responsive to purine nucleoside phosphorylase inhibition using said compounds or pharmaceutical compositions comprising said compounds of the invention.

7-(1-Substituted-hydroxyalkyl)-3,5-dihydropyrrolo[3,2-d]pyrimidin-4-ones, including specific 7-(1-aryl-3-hydroxypropyl)-substituted compounds, are, inter alia, disclosed in U.S. Patent 5,189,039 and International Application WO 93/21187. However, there is no suggestion to prepare the novel 7-(1-substituted-2-hydroxyethyl)-substituted compounds of the present invention to obtain unexpectedly potent PNP inhibitors.

The compounds of the invention are particularly useful in mammals as purine nucleoside phosphorylase (PNP) inihibitors, as selective inhibitors of T-cell formation and thus function as immunosuppressants suppressing cellular immunity. They can be used for the prevention and treatment of transplant rejection and for treatment of autoimmune diseases such as rheumatoid arthritis, psoriasis and dermatitis, Crohn's disease, uveitis, asthma, and diabetes in mammals. They can also be used to potentiate the antiviral and antitumor effect of antiviral or antitumor purine nucleosides, in particular 2',3'-dideoxypurine nucleosides for the treatment of retrovirus infections such as AIDS (acquired immunodeficiency syndrome); and also for the treatment of gout.

DETAILED DESCRIPTION OF THE INVENTION

The invention relates to the compounds of formula I

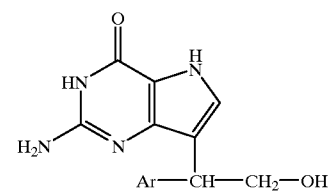

(I)

and tautomers thereof, wherein Ar represents biaryl, carbocyclic or heterocyclic aryl; pharmaceutically acceptable prodrug ester derivatives; and pharmaceutically acceptable salts thereof.

The compounds of the invention possess an asymmetric carbon atom and therefore exist as racemates and the (R) and (S) enantiomers thereof. The present invention is intended to include these forms, also diastereoisomers and mixtures thereof if two or more asymmetric centers are present.

Preferred are the enantiomers of formula Ia

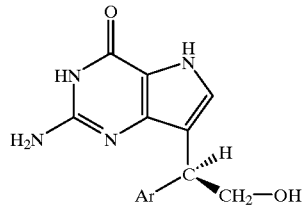

(Ia)

and tautomers thereof, wherein Ar represents biaryl, carbocyclic aryl or heterocyclic aryl; pharmaceutically acceptable prodrug ester derivatives thereof; and pharmaceutically acceptable salts thereof.

Embodiments of the invention are said compounds of formula I and Ia wherein Ar represents monocyclic carbocylic aryl or monocyclic heterocyclic aryl. A particular embodiment of the invention relates to the compounds of Formula I or Ia wherein Ar is phenyl or phenyl substituted by one to five substituents, preferably by one or two substituents. Preferred are the compounds of formula II and the corresponding enantiomers of formula IIa

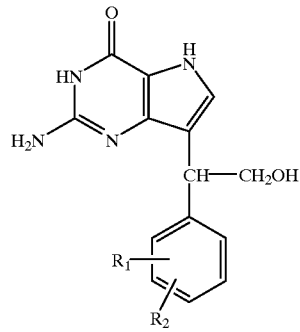

(II)

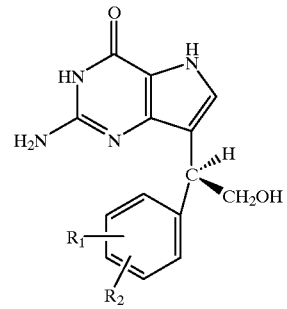

(IIa)

and tautomers thereof, wherein $R_1$ and $R_2$ represent independently hydrogen, halo, lower alkyl, hydroxy, lower alkoxy, aryl-lower alkoxy, acyloxy, aryloxy, trifluoromethyl, cyano, (hydroxy, lower alkoxy or acyloxy)-lower alkyl, or (lower alkylthio, lower alkylsulfinyl or lower alkylsulfonyl)-lower alkyl; or $R_1$ and $R_2$ together on adjacent carbon atoms represent lower alkylenedioxy; prodrug pharmaceutically acceptable ester derivatives thereof; and pharmaceutically acceptable salts thereof.

A further embodiment of the invention relates to the compounds of formula I and Ia wherein Ar is monocyclic heterocyclic aryl comprising thienyl, furanyl, pyridyl, pyrrolyl, thiazolyl, pyrazinyl, pyridazinyl or pyrazolyl.

Preferred are the compounds of formulae I and Ia and tautomers thereof, wherein Ar is phenyl, pyridyl or halophenyl such as chloro- or fluorophenyl; pharmaceutically acceptable carboxylic acid derived prodrug ester derivatives thereof; and pharmaceutically acceptable salts thereof.

Particularly preferred are the enantiomers of formula III

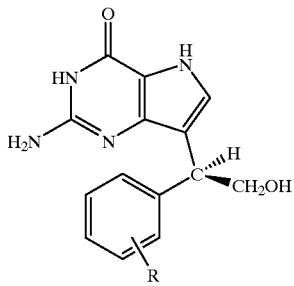

(III)

and tautomers thereof, wherein R represents hydrogen, chloro, or fluoro; pharmaceutically acceptable prodrug esters thereof; and pharmaceutically acceptable salts thereof.

Preferred in turn are the compounds of formula III wherein R is hydrogen or fluoro at the ortho position.

Further preferred embodiments of the invention relate to the specific compounds disclosed in the examples.

The compounds of the invention represent 9-substituted-9-deazaguanines which are named herein as 7-substituted 2-amino-3,5-dihydro-4H-pyrrolo[3,2-d]pyrimidin-4-ones. Such can exist in several tautomeric forms, e.g., as represented by structure IV.

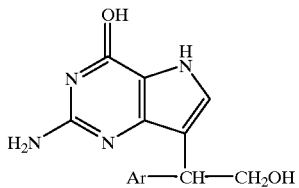

(IV)

and other structures involving allowable rearrangement of positions of double bonds. All tautomeric forms are within the scope of the invention.

The general definitions used herein have the following meaning within the scope of the present invention.

Aryl represents carbocyclic or heterocyclic aryl, either monocyclic or bicyclic.

Monocyclic carbocyclic aryl represents optionally substituted phenyl, being preferably phenyl or phenyl substituted by one to three substituents, such being advantageously lower alkyl, hydroxy, lower alkoxy, acyloxy, halogen, cyano, trifluoromethyl, carbocyclic aryloxy or carbocyclic aryl-lower alkoxy.

Bicyclic carbocyclic aryl represents 1- or 2-naphthyl or 1- or 2-naphthyl substituted by, e.g., lower alkyl, lower alkoxy or halogen.

Monocyclic heterocyclic aryl represents optionally substituted thienyl, furanyl, pyridyl, pyrrolyl, thiazolyl, pyrazinyl, pyridazinyl or pyrazolyl, preferably optionally substituted thiazolyl, thienyl, furanyl or pyridyl.

Optionally substituted furanyl represents 2- or 3-furanyl preferably substituted by lower alkyl.

Optionally substituted pyridyl represents 2-, 3- or 4-pyridyl or 2-, 3- or 4-pyridyl preferably substituted by lower alkyl, halogen or cyano.

Optionally substituted thienyl represents 2- or 3-thienyl or 2- or 3-thienyl preferably substituted by lower alkyl.

Optionally substituted thiazolyl represents, e.g., 4-thiazolyl, or 4-thiazolyl substituted by lower alkyl.

Bicyclic heterocyclic aryl represents preferably indolyl or benzothiazolyl optionally substituted by hydroxy, lower alkyl, lower alkoxy or halogen, advantageously 3-indolyl or 2-benzothiazolyl.

Aryl as in aryl-lower alkyl is preferably phenyl or phenyl substituted by one or two of lower alkyl, lower alkoxy, hydroxy, lower alkanoyloxy, halogen, trifluoromethyl or cyano; also, optionally substituted naphthyl.

Aryl-lower alkyl is advantageously benzyl or 1- or 2-phenethyl optionally substituted on phenyl by one or two of lower alkyl, lower alkoxy, hydroxy, lower alkanoyloxy, halogen, cyano or trifluoromethyl.

Biaryl represents phenyl substituted by carbocyclic aryl or heterocyclic aryl as defined herein, ortho, meta or para to the point of attachment of the phenyl ring, advantageously para, such as 4-biphenyl.

The term "lower" referred to herein in connection with organic radicals or compounds respectively defines such with up to and including 7, preferably up and including 4 and advantageously one or two carbon atoms. Such may be straight chain or branched.

A lower alkyl group preferably contains 1–4 carbon atoms and represents for example, ethyl, propyl, butyl or advantageously methyl.

A lower alkoxy group preferably contains 1–4 carbon atoms and represents for example, methoxy, propoxy, isoproproxy or advantageously ethoxy.

Halogen (halo) preferably represents fluoro or chloro, but may also be bromo or iodo.

Acyl is derived from a carboxylic acid and represents preferably optionally substituted lower alkanoyl, carbocyclic aryl-lower alkanoyl, aroyl, lower alkoxycarbonyl or aryl-lower alkoxycarbonyl, advantageously optionally substituted lower alkanoyl, or aroyl.

Lower alkanoyl is preferably acetyl, propionyl, butyryl, or pivaloyl.

Optionally substituted lower alkanoyl for example represents lower alkanoyl or lower alkanoyl substituted by lower alkoxycarbonyl, lower alkanoyloxy, lower alkanoylthio, lower alkoxy, or by lower alkylthio.

Aroyl is preferably monocyclic carbocyclic or monocyclic heterocyclic aroyl.

Monocyclic carbocyclic aroyl is preferably benzoyl or benzoyl substituted by lower alkyl, lower alkoxy, halogen or trifluoromethyl.

Monocyclic heterocyclic aroyl is preferably pyridylcarbonyl or thienylcarbonyl.

Acyloxy is preferably optionally substituted lower alkanoyloxy, lower alkoxycarbonyloxy, monocyclic carbocyclic aroyloxy or monocyclic heterocyclic aroyloxy.

Aryl-lower alkoxycarbonyl is preferably monocyclic carbocyclic-lower alkoxycarbonyl, advantageously benzyloxycarbonyl.

Pharmaceutically acceptable esters are preferably prodrug ester derivatives, such being convertible by solvolysis or under physiological conditions to the free alcohols of formula I.

Pharmaceutically acceptable prodrug esters of the alcohols of the invention are those derived from a carboxylic acid, a carbonic acid monoester or a carbamic acid, advantageously esters derived from an optionally substituted lower alkanoic acid or an arylcarboxylic acid.

The esters are represented by formula Ib

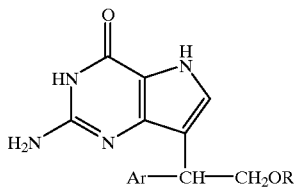

(Ib)

in which R represents acyl as defined herein. Such are convertible in vivo to the compounds of formula I.

Pharmaceutically acceptable salts represent acid addition salts with conventional acids, for example, mineral acids, e.g., hydrochloric acid, sulfuric or phosphoric acid, or organic acids, for example, aliphatic or aromatic carboxylic or sulfonic acids, e.g., acetic, propionic, succinic, glycolic, lactic, malic, tartaric, citric, ascorbic, maleic, fumaric, hydroxymaleic, pyruvic, pamoic, methanesulfonic, toluenesulfonic, naphthalenesulfonic, sulfanilic or cyclohexylsulfamic acid; also amino acids, such as arginine and lysine. For compounds of the invention having acidic groups, for example, a free carboxy group, pharmaceutically acceptable salts also represent metal or ammonium salts, such as alkali metal or alkaline earth metal salts, e.g., sodium, potassium, magnesium or calcium salts, as well as ammonium salts, which are formed with ammonia or suitable organic amines.

The compounds of the invention are particularly useful in mammals as purine nucleoside phosphorylase (PNP) inhibitors, e.g. for selectively suppressing T-cell mediated immunity in mammals, and for treating conditions in mammals in which T-cells are involved, e.g., autoimmune diseases, transplant rejection or psoriasis. Disorders considered to be of autoimmune origin include rheumatoid arthritis, systemic lupus erythematosus, myasthenia gravis, type I diabetes, multiple sclerosis, psoriasis and certain forms of dermatitis, Crohn's disease, uveitis, asthma and the like. The compounds of the invention are also useful for the treatment of gout.

The compounds of the invention are useful for inhibiting transplant rejection, e.g. for the treatment of transplant recipients (e.g., in heart, lung, combined heart-lung, liver, heart, kidney, pancreas, skin or corneal transplants), including both allo- and xeno-transplant rejection. The compounds of the invention are also indicated for the prevention of graft-versus-host disease, such as following bone marrow transplantation. For such indications the compounds of the invention may be used alone or in combination with known immunosuppressive agents. Such immunosuppressive agents include cyclosporine, tacrolimus, mycophenolic acid (mycophenolate mofetil), brequinar (brequinar sodium), rapamycin and the like. The dose of these agents required to achieve an immunosuppressive dose when used in combination may be lower, thus reducing the incidence of undesirable side effects associated with the particular known immunosuppressive agent, e.g., nephrotoxicity in the case of cyclosporin and tacrolimus.

The compounds of the invention are also useful for inhibiting the in vivo metabolic degradation of purine nucleosides via phosphorolysis, and are thus, useful to potentiate the antiviral and antitumor efficacy of 2' and/or 3'-mono- or dideoxypurine nucleosides. For instance, they are useful for potentiating e.g., 2',3'-dideoxyadenosine, 2',3'-dideoxyguanosine or 2',3'-dideoxyinosine for the treatment of retrovirus infections such as acquired immunodeficiency syndrome (AIDS). They are also useful for potentiating the antitumor/cytotoxic effect of e.g. 2'-deoxyguanosine in mammals.

The above-cited properties are demonstrable in vitro and in vivo tests using advantageously mammals, e.g., rats, mice, dogs, monkeys, and isolated cells thereof. Said compounds can be applied in vitro in the form of solutions, e.g., preferably aqueous solutions and in vivo either enterally or parenterally, advantageously orally and intravenously. The dosage in vitro may range between about $10^{-5}$ and $10^{-9}$ molar concentrations. The dosage in vivo may range, depending on the route of administration, between about 1 and 100 mg/kg.

PNP inhibition can be measured by measuring the formation of [$^{14}$C]-inosine [Biomedicine, 33, 39 (1980)] using calf spleen as the enzyme source and 1 or 50 mM phosphate. Results are expressed as $IC_{50}$ values, corresponding to the concentration of compound required to achieve a 50% reduction of the formation of hypoxanthine.

PNP inhibition can also be determined in vitro as follows: An enzymic method for the determination of inorganic phosphate (see Chem. Pharm. Bull., 1981, 29:1451–5), based on the principle of forming hydrogen peroxide with purine nucleoside phosphorylase (PNP) and xanthine oxidase, is used to calorimetrically measure the degree of linkage between enzyme and substrate (inosine). Calf spleen PNP is used as the enzyme source. The $IC_{50}$ values for the compounds studied are determined graphically at two phosphate concentrations (1 and 50 mM) from a plot of percent inhibition versus compound concentration.

Illustrative of the invention the compound of Example 1 and 3f have an $IC_{50}$ of about 10 nM at 1 mM phosphate concentration in this assay.

The selective suppression of spontaneous T-cell proliferation in vitro is measured by the potentiation of the cell growth inhibitory activity (cytotoxicity) of 2'-deoxyguanosine (d-Guo) by the compounds of the invention, determined as follows: Human CCRF-CEM cells are grown in RPMI-1640 medium. To suspension cultures of these cells, d-Guo at a fixed concentration (10 μM) and the candidate PNP inhibitor at varied concentrations are added and the number of cells are determined in a Coulter counter 24, 48, and 72 hours thereafter. From these data, the $IC_{50}$ is calculated as the concentration of PNP inhibitor required to reduce the increase in cell number between 0 and 72 hours to 50% of that of control cultures. This method is similar to that previously used to determine the effectiveness of PNP inhibitors on potentiation of the toxicity of d-Guo. [See D. A. Shewach et al., Cancer Res., 46, 519 (1986); J. C. Sircar et al., Agents and Actions, 21, 253 (1987), also Methods in Pharmacology, D. M. Paten, ed. 1985, pp. 147–162].

Illustrative of the invention the compounds of example 1 and 3f have an $IC_{50}$ of about 75 and 100 nM, respectively, in the CCRF-CEM cell assay.

PNP inhibition of the compounds of the invention can also be determined in vivo by demonstrating an increased level of the nucleoside inosine in mice (see Ann NY Acad. Sci., 1985, 451:313–4) when compared to vehicle treated mice. Briefly, mice are treated orally with the PNP inhibitor suspended in fortified cornstarch (3% cornstarch suspension in water with 0.33% Tween 80 and 5% PEG 400) at a final volume of 10 ml/kg. One or more hours after a single oral dose of compound, the mice are bled by cardiac puncture into 25 U/ml heparin to obtain plasma. The samples are analyzed for both inosine and drug levels by a gradient reverse-phase high performance liquid chromatography (HPLC) method (see Anal Chem, 1977, 49:2237–41). Quantitation is performed using an internal standard method with 2',3'-dideoxyinosine (DDI) as the internal standard.

Illustrative of the invention, the compound of example 1 and 3f cause a significant increase in the plasma level of inosine at a dose of e.g. 10 mg/Kg p.o.

The immunosuppressive activity can also be determined in further animal models of T-cell mediated immune responses such as experimental allergic encephalomyelitis, Freund's adjuvant or collagen-induced arthritis, and models of graft vs. host reactions.

The antiarthritic activity can be determined in the collagen II induced arthritis in mice model. DBA/1LacJ female mice, 6–8 weeks old, are immunized with 100 μg of chicken type II collagen emulsified in Freund's complete adjuvant (FCA) by injecting at the base of the tail on day 0. On day 17 after collagen injection, the immune response to type II collagen is boosted with a subcutaneous injection of 200 μg LPS solubilized in PBS. Paws are examined on days 17, 21, 24, 28, 31, 35, and 42 and scored for the symptoms of arthritis based on criteria such as inflammation, swelling and ankylosis. Compounds are suspended in corn starch vehicle and administered orally to mice once daily beginning on day 1 and continuing through day 42.

Illustrative of the invention, the compound of example 1 is effective at a dose of 20 mg/Kg/day.

Protection against transplant rejection can be determined in a mouse tail skin transplantation procedure.

Mice are anesthetized with tribromoethanol i.p. injection according to the method of Papaioannou and Fox (Lab. Animal Science 1993;43:189–92). The mouse tail skin transplant rejection model is a modification of that described by Baily and Usama, (Transpl. Bull. 1960;7:424–5). Four skin grafts per mouse are exchanged between strains [C57BL/10-SnJ (H-2K$^b$) and B10.BR/SgSnJ (H-2K$^k$)] at surgery (d0). Fitted skin grafts are made with a scalpel, and tail graft sites are protected with tubing for 2 days following surgery. Mouse tails are evaluated at day 7 for missing grafts. Only those graft sites that have patent grafts at day 7 are evaluated at later scoring intervals. Grafts are scored numerically for signs of rejection at ~weekly scoring intervals starting day 14. Dose-group mean graft scores are compared statistically. Drug treatment is considered efficacious if graft scores of compound treated mice are significantly lower than those of vehicle treated mice at days 20/21 and 27/28.

Illustrative of the invention, the compound of example 1 is effective in protecting against transplant rejection at a dose of 50 mg/Kg/day in the mouse.

Further illustrative of the invention, a combination of a compound of the invention, e.g. of example 1, and cyclosporin is superior to either cyclosporin or the PNP inhibitor alone in the transplant rejection model, thus leading to a reduction of the dose of cyclosporin and of the side effects associated therewith. Thus, the compounds of the invention have an immunosuppressant-sparing effect when administered in combination, e.g., a cyclosporin-sparing effect.

The compounds of the invention can be prepared by adaptation of previously reported synthetic methodology, e.g., M. I. Lim, R. S. Klein, and J. J. Fox, J. Org. Chem., 44, 3826 (1979); M. I. Lim., R. S. Klein, and J. J. Fox, Tetrahedron Lett., 21, 1013 (1980); M. I. Lim and R. S. Klein, Tetrahedron Lett., 22, 25 (1981); M. I. Lim. W. Y. Ren, B. A. Otter, and R. S. Klein, J. Org. Chem., 48, 780 (1983), as described below and illustrated in the examples.

For example, said compounds of the invention are prepared by treating a compound of the formula

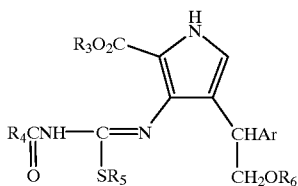

(V)

wherein Ar has meaning as previously defined, $R_3$ represents lower alkyl, $R_4$ represents carbocyclic aryl, $R_5$ represents lower alkyl, and $R_6$ represents an O-protecting group, with anhydrous ammonia; and if required converting a resulting compound of formula I into another compound of the invention.

Lower alkyl as defined for $R_3$ and $R_5$ represents $C_1$–$C_7$-alkyl, advantageously methyl or ethyl.

Carbocyclic aryl as defined for $R_4$ represents advantageously phenyl.

An O-protecting group as defined for $R_6$ represents, e.g., tetrahydropyranyl, benzyl, trityl and the like.

The condensation of an intermediate of formula V with ammonia and cyclization to a compound of the invention, e.g., of formula I, II or III is preferably carried out in a polar inert non-aqueous solvent such as a lower aliphatic alcohol, advantageously methanol, preferably at elevated temperature, e.g., 80–100° C. under pressure in a closed vessel.

The starting materials of the formula V are advantageously prepared by first treating a pyrrole derivative of the formula VI

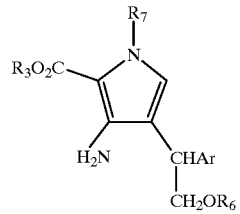

(VI)

wherein Ar, $R_3$ and $R_6$ have meaning as defined herein, and $R_7$ represents hydrogen or lower alkoxycarbonyl, with a carbocyclic aroyl isothiocyanate, advantageously benzoyl isothiocyanate, in an inert solvent such as dichloromethane to yield a compound of the formula VII

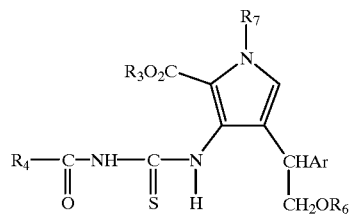

(VII)

wherein Ar, $R_3$, $R_4$, $R_6$ and $R_7$ have meaning as defined above.

Subsequent condensation of intermediates of formula VII with a reactive derivative of a lower alkylcarbinol, e.g., a lower alkyl halide, advantageously methyl iodide, in an inert solvent such as methylene chloride, in the presence of an organic or inorganic base, e.g., an amine such as 1,5-diazabicyclo [4.3.0]non-5-ene (DBN) yields intermediates of formula V.

The pyrrole starting materials of formula VI can be prepared similarly to methodology described in the art for the synthesis of 3-amino-4-substituted-2-pyrrolecarboxylic acids and esters thereof, e.g., as described in J. Org. Chem. 44, 3826 (1979), and as particularly illustrated herein.

Said pyrrole compounds are advantageously prepared as illustrated below for compounds of formula VI wherein $R_3$ represents methyl.

sponding β-(hydroxymethyl)-β-arylpropionitrile with a reducing agent suitable for the selective reduction of an ester, such as lithium or sodium borohydride.

The optically active β-hydroxymethyl-β-arylpropionitriles can be advantageously prepared as follows:

The appropriate arylacetic acid, preferably in form of an acid chloride is condensed with the appropriate optically active (R)-4-monosubstituted-2-oxazolidinone (e.g. 4(R)-phenyl-2-oxazolidinone) in the presence of a strong base, such as n-butyl lithium or potassium t-amylate, under conditions well-known in the art to obtain the corresponding enantiomer, 3-(arylacetyl)-4-(R)-substituted-2-

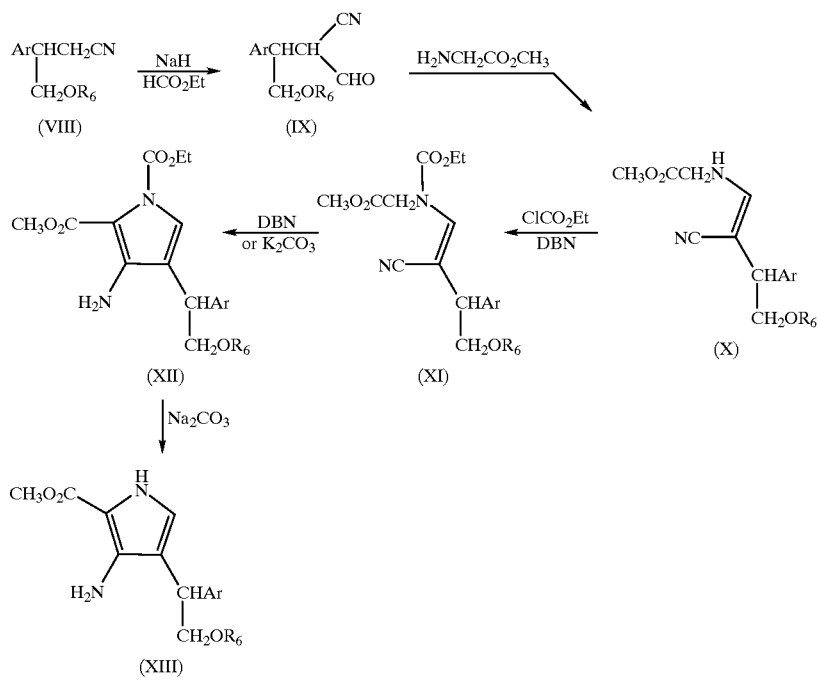

Ar in the above compounds has meaning as previously defined herein.

The 3-substituted-3-arylpropionitrile VIII is condensed with ethyl formate in the presence of e.g. sodium hydride in anhydrous tetrahydrofuran to yield the corresponding 2-formyl-3-arylpropionitrile IX which is in turn condensed with glycine methyl ester in the presence of e.g. sodium acetate to yield the enamine of formula X. The enamine of formula X is in turn N-protected with ethyl chloroformate and the resulting N-ethoxycarbonyl derivative XI is cyclized in the presence of a base, e.g., DBN or $K_2CO_3$, to yield the N-protected pyrrole of formula XII. The intermediate of formula XI is formed in situ and usually not isolated. Deprotection by treatment with e.g. sodium carbonate in methanol yields the starting material of formula VI wherein $R_7$ represents hydrogen.

The β-hydroxymethyl-β-arylpropionitriles of formula VIII ($R_6$ being H) are either known in the art or are prepared according to methodology known in the art, and are then O-protected using methods well-known in the art.

Such are typically prepared by condensing the appropriate arylacetic acid ester with, for example, bromoacetonitrile in the presence of a strong base, e.g., lithium diethylamide to obtain the corresponding β-(lower alkoxycarbonyl)-β-arylpropionitrile which is selectively reduced to the correoxazolidinone. This is in turn condensed with bromoacetonitrile in the presence of, e.g. lithium or sodium hexamethyldisilazide to give the corresponding optically active 3-(β-cyano-α-arylpropionyl)-4-(R)-substituted-2-oxazolidinone which is reduced with lithium borohydride or sodium borohydride to give the corresponding enantiomer of an alcohol of formula VII wherein $R_6$ is hydrogen, namely of β-(hydroxymethyl)-β-arylpropionitrile. The other enantiomer is similarly prepared.

Alternatively, the compounds of formula I are prepared by condensing an intermediate of formula VI with cyanamide, optionally in a polar solvent such as ethanol or isopropanol, preferably in a sealed system, at elevated temperature such as about 100–150° C., in the presence of acid, e.g., concentrated hydrochloric acid.

As a modification thereof, an intermediate of formula VI (wherein $R_7$ is hydrogen) is first treated with aqueous acid to remove the O-protecting group $R_6$, followed by treatment with cyanamide in the presence of acid, e.g. hydrochloric acid, optionally followed by treatment with base, e.g. sodium hydroxide, to obtain a compound of formula I.

An illustrative reaction sequence for the converstion of an optically active protected β-hydroxymethyl-β-arylpropionitrile (wherein $R_6$ is e.g. trityl) to a compound of formula Ia is illustrated below.

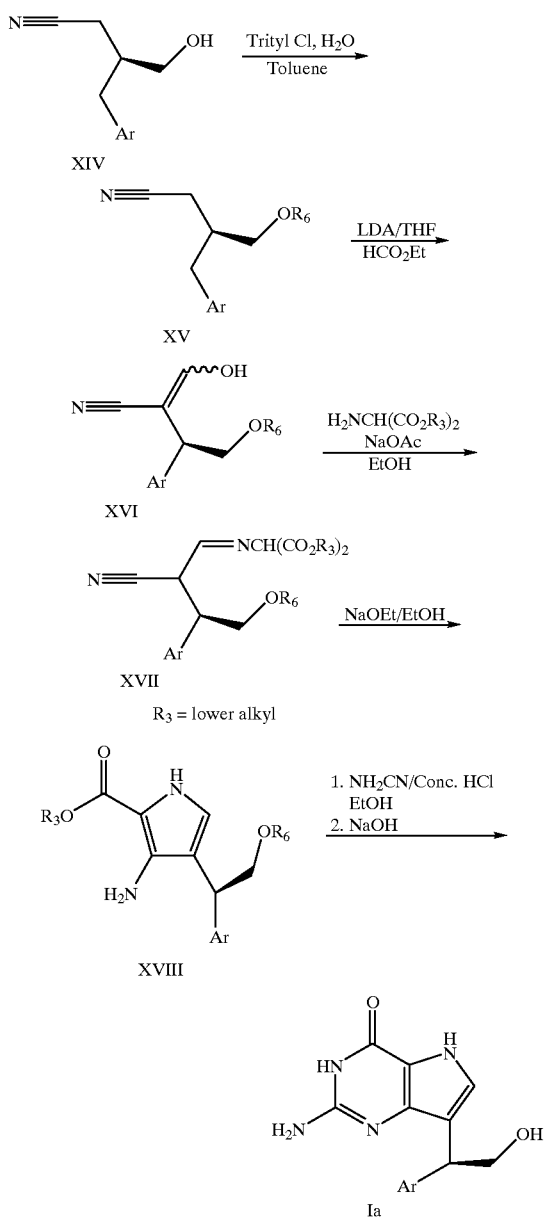

The β-hydroxymethyl-β-arylpropionitrile XIV is first converted to the O-protected derivative XV (wherein $R_6$ is e.g. trityl) which is treated with ethyl formate in the presence of a strong base, such as lithium diisopropylamide, to give the α-formyl-β-arylpropionitrile of formula XVI. Such is treated with an amino malonic dialkyl ester, e.g. diethyl amino-malonate, to yield an imine compound of formula XVII. Treatment with a strong base results in cyclization to a pyrrole of formula XVIII. Finally, condensation of the pyrrole intermediate with cyanamide, in acid (such as concentrated HCl) followed by base (such as sodium hydroxide) yields a corresponding compound of formula Ia.

In summary, the compounds of formula 1, as substantially pure enantiomers, are prepared by:

(a) condensing a compound of the formula

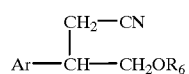
(XIX)

as a substantially pure enantiomer, wherein Ar has meaning as defined above and $R_6$ is an O-protecting group with a lower alkyl ester of formic acid to obtain a compound of the formula

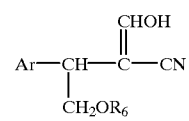
(XX)

as a substantially pure enantiomer;

(b) then condensing the compound so obtained with a compound of the formula

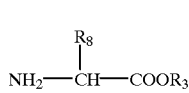
(XXI)

wherein $R_8$ is hydrogen or $COOR_3$ and $R_3$ is lower alkyl, to obtain a compound of the formula

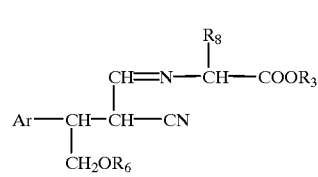
(XXII)

or an enamine tautomer thereof, as a substantially pure enantiomer;

(c) then cyclizing the compound so obtained to a compound of the formula

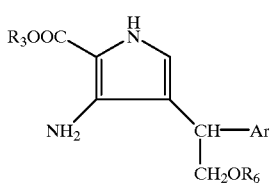
(XXIII)

as a substantially pure enantiomer;

(d) and then condensing the compound so obtained
  (1) with a carbocyclic aroyl isothiocyanate and treatment of the product so obtained with an alkyl halide followed by anhydrous ammonia; or
  (2) with cyanamide in acid, optionally followed by treatment with a base.

As noted above in the cited processes, such may be carried out while, if necessary, temporarily protecting any interfering reactive group(s), and then liberating the resulting compound of the invention.

In starting compounds and intermediates which are converted to the compounds of the invention in a manner described herein, functional groups present, such as hydroxy groups, are optionally protected by conventional protecting groups that are a common in preparative organic chemistry.

Well-known protecting groups and their introduction and are described, for example, in J. F. W. McOmie, "Protective Groups in Organic Chemistry", Plenum Press, London, N.Y., T. W. Greene, "Protective Groups in Organic Synthesis", Wiley, N.Y. For example, a hydroxy group is advantageously protected in the form of a benzyl ether which can be cleaved by catalytic hydrogenation to obtain a hydroxy substituted product.

The above-mentioned reactions are carried out according to standard methods, in the presence or absence of diluent, preferably such as are inert to the reagents and are solvents thereof, of catalysts, condensing or said other agents respectively and/or inert atmospheres, at low temperatures, room temperature or elevated temperatures (preferably at or near the boiling point of the solvents used), and at atmospheric or super-atmospheric pressure. The preferred solvents, catalysts and reaction conditions are set forth in the appended illustrative examples.

Advantageously those starting materials are used in said reactions that lead to the formation of those compounds indicated above as being preferred.

The invention also relates to any novel starting materials and processes for their manufacture.

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

The compounds of the invention or intermediates can also be obtained in the form of their hydrates, or include other solvents used for their crystallization.

The invention further relates to pharmaceutical compositions suitable for enteral, such as oral or rectal, transdermal and parenteral administration to mammals including man, which are useful to inhibit purine nucleoside phosphorylase activity and for the treatment of disorders responsive thereto, comprising an effective amount of a pharmacologically active compound of the invention, alone or in combination, with one or more pharmaceutically acceptable carriers.

Preferred pharmaceutical compositions are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g. starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50% of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

The invention further relates to a method of inhibiting purine nucleoside phosphorylase activity in mammals and treating diseases and conditions responsive thereto, e.g. autoimmune disorders, rejection of transplantation or psoriasis, which comprises administering to a mammal in need thereof an effective amount of a compound of the invention or of a pharmaceutical composition comprising a said compound in combination with one or more pharmaceutically acceptable carriers.

A particular embodiment thereof relates to a method of selectively suppressing T-cell function and cellular immunity in mammals which comprises administering to a mammal in need thereof a correspondingly effective inhibiting amount of a compound of the invention or of a said compound in combination with one or more pharmaceutically acceptable carriers.

A further embodiment of the invention relates to a method of inhibiting the phosphorolysis and metabolic breakdown of antiviral or antitumor purine nucleosides in mammals which comprises administering in conjunction therewith to a mammal in need thereof, either separately or in combination therewith, an effective purine nucleoside phosphorylase inhibiting amount of a compound of the invention or of a said compound in combination with one or more pharmaceutically acceptable carriers. More particularly, such relates to a method of inhibiting the phosphorolysis and metabolic breakdown of purine nucleosides known in the art, e.g., of 2'-deoxyguanosine, 2'-3'-dideoxyinosine, 2'3'-dideoxyguanosine or 2'-3'-dideoxyadenosine.

Furthermore, the invention thus relates to a method of potentiating the antiviral or antitumor effect of 2' or 3'-monodeoxypurine nucleosides or of 2',3'-dideoxypurine nucleosides in mammals which comprises administering in conjunction therewith to a mammal in need thereof, either separately or in combination with a said nucleoside, an effective purine nucleoside phosphorylase inhibiting amount of a compound of the invention preferably in combination with one or more pharmaceutically acceptable carriers. More particularly, such relates to a method of enhancing or potentiating the effect of 2',3'-dideoxypurine nucleosides known in the art, e.g., of 2',3'-dideoxyadenosine for the treatment of retrovirus infections, e.g. HIV-retrovirus infections (acquired immunodeficiency syndrome, AIDS). 2',3'-Dideoxypurine nucleosides are known in the art as inhibitors of HIV retrovirus infectivity and to be metabolically degraded by PNP, e.g., as described in Biochemical Pharmacology 22, 3797 (1987). Such area administered at a pharmaceutically acceptable dose which is effective in inhibiting HIV-retrovirus infections. Preferably the lowest possible effective dose is used.

The pharmaceutically acceptable effective dosage of active compound of the invention to be administered is dependent on the species of warm-blooded animal (mammal), the body weight, age and individual condition, and on the form of administration.

A unit dosage for a mammal of about 50 to 70 kg may contain between about 1 and 150 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. The structure of final products, intermediates and starting materials is confirmed by standard analytical methods, e.g. microanalysis and spectroscopic characteristics (such as MS, IR, NMR and UV).

Depending on the chemical nature of the substituent at the asymmetric carbon, an enantiomer having the configuration depicted in formula Ia, IIa or III, is according to conventional rules of nomenclature, named (R) or (S). If such enantiomer is (R), then the corresponding antipode would be called (S).

EXAMPLE 1

To a solution of 2-amino-7-[1-(2-fluorophenyl)-2(R)-[(tetrahydropyran-2-yl)oxy]ethyl]-3,5-dihydro-4H-pyrrolo[3,2-d]pyrimidin-4-one (30 g, 0.08 mol) in MeOH (500 mL) is added 2N HCl (50 mL). The reaction mixture is stirred at ambient temperature for ~3 hours. The resulting solution is neutralized with saturated NaHCO$_3$ solution (100 mL) and H$_2$O (500 mL) is added after which the mixture is stirred for 30 minutes. The white solid which precipitates is then collected and washed with H$_2$O (2×20 mL) and Et$_2$O (2×20 mL) to provide 2-amino-7-[1-(2-fluorophenyl)-2(R)-hydroxyethyl]-3,5-dihydro-4H-pyrrolo[3,2-d]pyrimidin-4-one, m.p. 263–264° C., of the formula

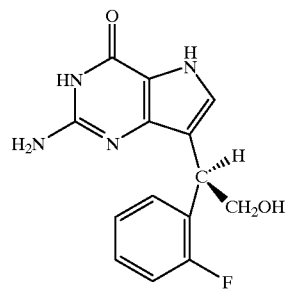

The starting material is prepared as follows:

To a solution of 2-fluorophenylacetic acid (450 g, 3.0 mol) in CH$_2$Cl$_2$ (900 mL) is added SOCl$_2$ (714 g, 6 mol) dropwise. After addition is complete, the reaction mixture is heated to reflux for 2 hours. Subsequently, the solvent is removed in vacuo after which vacuum distillation of the resulting oil provides 2-fluorobenzeneacetyl chloride.

To a −78° C. solution of 4(R)-phenyl-2-oxazolidinone (340 g, 2.08 mol) in THF ( 8000 mL), is added n-BuLi (2.5 M, 920 mL, 1.1 eq). The reaction mixture is stirred for 20 minutes and 2-fluorobenzeneacetyl chloride (358 g, 2.08 mol) is added. After 2 hours the reaction mixture is quenched with saturated NH$_4$Cl solution (1×1000 mL). The organic layer is separated, washed with H$_2$O (1×1000 mL), saturated NaCl solution ( 2×1000 mL) and then concentrated in vacuo. This procedure yields 3-[(2-fluorophenyl)-acetyl]-4(R)-phenyl-2-oxazolidinone.

To a solution of 3-[(2-fluorophenyl)-acetyl]-4(R)-phenyl-2-oxazolidinone (435 g, 1.45 mol) in THF (6000 mL), is added sodium hexamethyldisilazide [(TMS)$_2$ NNa, 1M in THF, 1480 ml, 1.48 mol] dropwise at −78° C. The resulting mixture is then warmed to −30° C. and stirred for 2.5 hours. After this time the reaction mixture is recooled to −78° C. and a solution of BrCH$_2$CN (175 g, 1.46 mmol) in THF (200 mL) is added. The reaction mixture is then warmed to −40° C. and stirred for 2 hours. Subsequently the resulting solution is treated with saturated NH$_4$Cl (1×3000 ml) and extracted with EtOAc (1×3000 mL). The organic layer is separated, washed with H$_2$O (1×1500 mL), saturated NaCl solution (2×1500 mL), dried over MgSO$_4$ and concentrated in vacuo, to provide 3-[(R)-β-cyano-α-(2-fluorophenyl)-propionyl]-4-(R)-phenyl-2-oxazolidinone, m.p. 179–181° C.

3-[(R)-β-Cyano-α-(2-fluorophenyl)-propionyl]-4-(R)-phenyl-2-oxazolidinone (400 g, 1.18 mol) is suspended in THF (4000 mL) and H$_2$O (25 mL). The reaction mixture is cooled in ice bath to 0° C. and a solution of LiBH$_4$ in THF (2M, 887 ml, 1.77 mol, 1.5 eq) is added slowly. The mixture is then stirred at 0° C. for 2 hours, after which 2N HCl (1500 mL) is cautiously added. The resulting solution is then extracted with Et$_2$O (2×1500 mL). The combined organic phases are then washed with saturated NaCl solution (2×1500 mL), dried over MgSO$_4$ and concentrated in vacuo. The solid 4(R)-phenyl-2-oxazolidinone is recovered by filtration and washed with Et$_2$O (2×100 mL). The filtrate is then chromatographed (silica gel, EtOAc/Hexanes, 1:3 ) to give β(R)-(hydroxymethyl)-β-(2-fluorophenyl)-propionitrile as an oil.

To a solution of β(R)-(hydroxymethyl)-β-(2-fluorophenyl)-propionitrile (210 g, 1.18 mol) in Et$_2$O (200 ml), is added 3,4-dihydro-2H-pyran (225 ml, 2.68 mol) at ambient temperature. The mixture is stirred for 5 minutes and POCl$_3$ (5 mL) is added dropwise. The reaction mixture is stirred for 30 minutes at ambient temperature and then refluxed for 2 hours. The resulting solution is allowed to cool and the solvent is removed in vacuo. The residue is then chromatographed (EtOAc/hexane, 1:4) to give β(R)-[[(tetrahydropyran-2-yl)oxy]methyl]-β-(2-fluorophenyl)-propionitrile as an oil.

To a 0° C. solution of β(R)-[[(tetrahydropyran-2-yl)oxy]methyl]-β-(2-fluorophenyl)propionitrile (240 g, 0.91 mol) in Et$_2$O (3000 mL) and hexane (3000 mL), is added NaH (60%, 127 g, 3.2 mol, 3.5 eq) and the resulting mixture is stirred for 30 minutes. Ethyl formate (540 g, 7.3 mol. 8 eq) is added and the reaction mixture is stirred at 0° C. for 1 hour. The cooling bath is removed and the mixture is stirred at ambient temperature for two days. After this time water (3000 mL) is added and the aqueous phase is washed with hexane (2×1000 mL), after which the pH is adjusted to between 6~7 with 1N HCl. Subsequently the aqueous phase is extracted with Et$_2$O (5×400 mL) and the combined organics washed with brine (2×2000 mL), dried over MgSO$_4$ and concentrated in vacuo. This provides α-(hydroxymethylidenyl)-β(R)-[(tetrahydropyran-2 -yloxy)methyl]-β-(2-fluorophenyl)-propionitrile which is used without purification for the next reaction.

To a solution of α-(hydroxymethylidenyl)-β(R)-[(tetrahydropyran-2-yl-oxy)-methyl]-β-(2-fluorophenyl)-propionitrile (261 g, 0.90 mol) in MeOH (4000 mL) and H$_2$O (700 mL), is added glycine methyl ester hydrochloride (226 g, 1.80 mol, 2 eq) and NaOAc (185 g, 2.25 mol, 2.5 eq). The reaction mixture is stirred at ambient temperature for 2 hours, and then the solvent is removed in vacuo. The resulting material is then dissolved in EtOAc (2×1000 mL). The ethyl acetate solution is then washed with H$_2$O (1×1000 mL), saturated NaCl solution (2×1000 mL) and dried over MgSO$_4$. Subsequently, the solvent is removed in vacuo to give α-[[(carbomethoxymethyl)-amino]methylidenyl]-β(R)-[(tetrahydropyran-2-yloxy)-methyl]-β(2-fluorophenyl)-propionitrile.

To a 0° C. solution of a-[[(carbomethoxymethyl)amino]methylidenyl]-β(R)-[(tetrahydropyran-2-yloxy)methyl]-β

(2-fluorophenyl)-propionitrile (320 g, 0.88 mol) in CH$_2$Cl$_2$ (1500 mL), is added a solution of DBU (305.8 g, 2.46 mol, 2.8 eq) in CH$_2$Cl$_2$ (500 mL). Subsequently a solution of ethyl chloroformate (219 g, 2.02 mol, 2.3 eq) in CH$_2$Cl$_2$ (500 mL) is slowly added. The reaction mixture is allowed to warm to ambient temperature and is stirred for ~12 hr. Water (2000 mL) is added and the aqueous phase extracted with CH$_2$Cl$_2$ (1×1000 mL). The organic layer is washed with H$_2$O (1×2000 mL), saturated NaCl solution (2×2000 mL) and dried over MgSO$_4$. The solvent is then removed in vacuo to provide ethyl methyl 3-amino-4-[1-(2-fluorophenyl)-2(R)-[(tetrahydropyran-2-yloxy)ethyl]-1H-pyrrole-1,2-dicarboxylate as an oil.

A suspension of ethyl methyl 3-amino-4-[1-(2-fluorophenyl)-2(R)-[(tetrahydropyran-2-yloxy)ethyl]-1H-pyrrole-1,2-dicarboxylate (300 g, 0.69 mol) and K$_2$CO$_3$ (170 g, 1.23 mol) in MeOH (2500 mL) is stirred for ~12 hour at ambient temperature. The reaction mixture is filtered, and the solid is washed with EtOAc (2×100 mL). The combined organic washings are then treated with H$_2$O (1×1000 mL), saturated NaCl solution (2×1000 mL), dried over MgSO$_4$ and concentrated in vacuo. The resulting material is chromatographed (EtOAc:hexane, 1:3) to give methyl 3-amino-4-[1-(2-fluorophenyl)-2(R)-[(tetrahydropyran-2-yloxy) ethyl]-1H-pyrrole-2-carboxylate.

To a 0° C. solution of methyl 3-amino-4-[1-(2-fluorophenyl)-2(R)-[(tetrahydropyran-2-yloxy)ethyl]-1H-pyrrole-2-carboxylate (150 g, 0.41 mol) in CH$_2$Cl$_2$ (1300 mL) is added a solution of benzoyl isothiocyanate (150 g, 0.92 mol) in CH$_2$Cl$_2$ (200 mL). The reaction mixture is allowed to warm to ambient temperature and is stirred for ~12 hours. The solvent is removed in vacuo and the residue chromatographed (EtOAc:hexane, 1:2) to provide methyl 3-[benzoyl[amino(thioxomethylamino)]]-4-[1-(2-fluorophenyl)-2(R)-[(tetrahydropyran-2-yloxy)ethyl]-1H-pyrrole-2-carboxylate as an oil.

To a 0° C. solution of methyl 3-[benzoyl[amino (thioxomethylamino)]]-4-[1-(2-fluorophenyl)-2(R)-[{(tetrahydropyran-2-yl}oxy)ethyl]-1H-pyrrole-2-carboxylate (180 g, 0.35 mol) in CH$_2$Cl$_2$ (3000 mL) is added MeI (100 g, 0.70 mol, 2 eq) and a solution of DBN (100 g, 0.80 mol, 2.3 eq) in CH$_2$Cl$_2$ (500 mL). The mixture is stirred at 0° C. for 1 hour and then allowed to warm to ambient temperature. After an additional hour the solvent is removed in vacuo, and the residue chromatographed (EtOAc: hexane, 1:3) to provide methyl 3-[(benzoylamino) (methylthio) methyleneimino]-4-[1-(2-fluorophenyl)-2(R)-[(tetrahydropyran-2-yloxy)ethyl]-1H-pyrrole-2-carboxylate.

Methyl 3-[(benzoylamino) (methylthio)methyleneimino]-4-[1-(2-fluorophenyl)-2(R)-[(tetrahydropyran-2-yloxy) ethyl]-1H-pyrrole-2-carboxylate (80 g, 0.148 mol) is dissolved in MeOH (2000 mL) and the resulting solution is placed in a high pressure containment vessel. The vessel is chilled in an ice/MeOH bath and NH$_3$ gas is passed through the reaction mixture for 40 minutes. After this time CH$_3$ONa (80 g, 1.48 g, 10 eq) is added to the NH$_3$/MeOH solution and the vessel is sealed and heated to 100° C. for 10 hours. The reaction mixture is then cooled to ambient temperature and is stirred for ~12 hours. The vessel is cooled to 0° C. before being opened, and the reaction mixture is then diluted with H$_2$O (1000 mL), after which the excess ammonia and methanol are removed in vacuo. The resulting solution is extracted with EtOAc (2×500 mL), treated with saturated NH$_4$Cl (~2000 mL) and once again extracted with EtOAc (2×1000 mL). The combined organic layers are washed with water (2×500 mL), saturated NaCl solution (2×500 mL) and dried over MgSO$_4$. The solvent is removed in vacuo and the residue chromographed (silica gel, EtOAc:MeOH, 95:5) to obtain 2-amino-7-[1-(2-fluorophenyl)-2(R)-(tetrahydropyran-2-yloxy)ethyl]-3,5-dihydro-4H-pyrrolo[3,2-d]pyrimidin-4-one.

EXAMPLE 2

Similarly prepared to procedure of example 1 is 2-amino-3,5-dihydro-7-[(2-hydroxy-1-phenyl)ethyl]-4H-pyrrolo[3,2-d]pyrimidin-4-one, m.p. 163–166° C.

The racemic β-(hydroxymethyl)-β-phenylpropionitrile intermediate is prepared as follows:

A solution of methyl phenylacetate (200 g, 1.33 mol) in THF (300 mL) is added, dropwise, to a −78° C. solution of lithium diethylamide (LDA, 1.4 mol) in THF (2500 mL). After addition is complete, a precipitate forms, and additional THF (200 mL) is added. The resulting mixture is vigorously stirred while a solution of bromoacetonitrile (168 g, 1.4 mol) in THF (400 mL) is slowly added. After 20 minutes the cooling bath is removed and the reaction mixture is quenched with saturated NH$_4$Cl solution (500 mL). After allowing the mixture to slowly warm to ambient temperature any solid material is removed by filtration and the solvent is removed in vacuo. The residue is dissolved in ET$_2$O (1000 mL) and diluted with H$_2$O (1000 mL). The organic phase is then washed with 0.5N HCl (1×1000 mL), saturated NaCl solution (2×1000 mL) and concentrated in vacuo. The residue is then vacuum distilled (~1 mm Hg) and the fraction boiling between 125° C. and 145° C. is collected to give β-(carbomethoxy)-β-phenylpropionitrile which solidifies upon standing.

β-(Carbomethoxy)-β-phenylpropionitrile (144 g, 0.76 mol) is dissolved in dimethoxyethane (1500 mL) and NaBH$_4$ (63.5 g, 1.67 mol) is cautiously added. The reaction mixture is stirred for 30 minutes and then heated at reflux for 2 hours. After this time the resulting solution is allowed to cool to ambient temperature and is poured onto ice. The mixture is then treated with 2N HCl (1500 mL) and is subsequently diluted with Et$_2$O (1500 mL). The organic phase is washed with H$_2$O (1×1000 mL), saturated NaCl solution (2×1000 mL), dried over MgSO$_4$ and concentrated in vacuo to yield β-(hydroxymethyl)-β-phenylpropionitrile.

EXAMPLE 3

The following compounds are prepared as described in previous examples from the appropriate corresponding propionitrile derivative.
(a) 2-Amino-7-[1-(4-chlorophenyl)-2-hydroxyethyl]-3,5-dihydro-4H-pyrrolo[3,2-d]-pyrimidin-4-one, m.p. 201–203° C.
(b) 2-Amino-7-[1-(3,4-dichlorophenyl)-2-hydroxyethyl]-3,5-dihydro-4H-pyrrolo-[3,2-d]pyrimidin-4-one, m.p.>220° C.
(c) 2-Amino-7-[1-(4-fluorophenyl)-2-hydroxyethyl]-3,5-dihydro-4H-pyrrolo[3,2-d]-pyrimidin-4-one, m.p. 266° dec.
(d) 2-Amino-7-[1-(3-chlorophenyl)-2-hydroxyethyl]-3,5-dihydro-4H-pyrrolo[3,2-d]-pyrimidin-4-one, m.p. 253–255° C.
(e) 2-Amino-7-(2(R)-hydroxy-1-phenylethyl)-3,5-dihydro-4H-pyrrolo[3,2-d]-pyrimidin-4-one, m.p. 203–205° C.
(f) 2-Amino-7-(2(S)-hydroxy-1-phenylethyl)-3,5-dihydro-4H-pyrrolo[3,2-d]-pyrimidin-4-one, m.p.>249–250° C.
(g) 2-Amino-3,5-dihydro-7-[2-hydroxy-1-(2-methoxyphenyl)ethyl]-4H-pyrrolo[3,2-d]-pyrimidin-4-one, m.p. 262–265° C.

(h) 2-Amino-3,5-dihydro-7-[2-hydroxy-1-(2-trifluoromethylphenyl)-ethyl]-4H-pyrrolo[3,2-d]pyrimidin-4-one, m.p. 247–250° C.

(i) 2-Amino-3,5-dihydro-7-[2-hydroxy-1-[(3-phenoxyphenyl)ethyl]-4H-pyrrolo[3,2-d]-pyrimidin-4-one, m.p. 250–252° C.

(j) 2-Amino-3,5-dihydro-7-[2-hydroxy-1-[(3-trifluoromethylphenyl)ethyl]-4H-pyrrolo[3,2-d]pyrimidin-4-one, m.p. 267–272° C.

(k) 2-Amino-3,5-dihydro-7-[2-hydroxy-1-[(3,4-dimethoxyphenyl)ethyl]-4H-pyrrolo[3,2-d]pyrimidin-4-one, m.p. 267–270° C.

(l) 2-Amino-3,5-dihydro-7-[2-hydroxy-1-(2-naphthalenyl)ethyl]-4H-pyrrolo[3,2-d]-pyrimidin-4-one, m.p. 268–272° C.

(m) 2-Amino-3,5-dihydro-7-[2-hydroxy-1-[4-(1-methylethyl)phenyl]ethyl]-4H-pyrrolo[3,2-d]pyrimidin-4-one, m.p. >300° C.

(n) 2-Amino-7-[1-(1,3-benzodioxol-5-yl)-2-hydroxyethyl]-3,5-dihydro-4H-pyrrolo[3,2-d]pyrimidin-4-one, m.p.>300° C.

(o) 2-Amino-3,5-dihydro-7-[2-hydroxy-1-(4-methoxyphenyl)ethyl]-4H-pyrrolo[3,2-d]pyrimidin-4-one, m.p. 275–285° C.

(p) 2-Amino-3,5-dihydro-7-[2-hydroxy-1-(4-trifluoromethylphenyl)ethyl]-4H-pyrrolo[3,2-d]pyrimidin-4-one, m.p. 201–202° C.

(q) 2-Amino-3,5-dihydro-7-[2-hydroxy-1-(3-methoxyphenyl)ethyl]-4H-pyrrolo[3,2-d]-pyrimidin-4-one, m.p. 275° C.

(r) 2-Amino-7-[1-(biphenyl-4-yl)-2-hydroxyethyl]-3,5-dihydro-4H-pyrrolo[3,2-d]-pyrimidin-4-one, m.p. >300° C.

(s) 2-Amino-3,5-dihydro-7-[1-(2,5-dimethoxyphenyl)-2-hydroxyethyl]-4H-pyrrolo[3,2-d]pyrimidin-4-one, m.p. 249–250° C.

(t) 2-Amino-7-[1-(3-fluorophenyl)-2-hydroxyethyl]-3,5-dihydro-4H-pyrrolo[3,2-d]-pyrimidin-4-one, m.p. 202–205° C.

(u) 2-Amino-7-[1-(3-fluorophenyl)-2(S)-hydroxyethyl]-3,5-dihydro-4H-pyrrolo[3,2-d]-pyrimidin-4-one, m.p. 220–222° C.

(v) 2-Amino-7-[-(4-fluorophenyl)-2(S)-hydroxyethyl]-3,5-dihydro-4H-pyrrolo[32-d]-pyrimidin-4-one, m.p. 254–256° C.

(w) 2-Amino-3,5-dihydro-7-(2(S)-hydroxy-1-phenylethyl)-4H-pyrrolo[3,2-d]pyrimidin-4-one, monohydrochloride, m.p. 290–295° C.

(x) 2-Amino-3,5-dihydro-7-[2-hydroxy-1-(3-methylphenyl)ethyl]-4H-pyrrolo[3,2-d]-pyrimidin-4-one, m. p. 248–249° C.

(y) 2-Amino-3,5-dihydro-7-[2-hydroxy-1-[2-(4-hydroxybutyl)phenyl]ethyl]-4H-pyrrolo[3,2-d]pyrimidin-4-one, m.p. 163–165° C.

(z) 2-Amino-3,5-dihydro-7-[2-hydroxy-1-[3-(phenylmethoxy)phenyl]ethyl]-4H-pyrrolo[3,2-d]pyrimidin-4-one, m.p. 235–236° C.

(aa) 2-Am ino-3,5-dihydro-7-[2-hydroxy-1-(3-hydroxyphenyl)ethyl]-4H-pyrrolo[3,2-d]-pyrimidin-4-one, monohydrochloride, m.p. 195° dec.

(bb) 2-Amino-3,5-dihydro-7-[2-hydroxy-1-(2-hydroxyphenyl)ethyl]-4H-pyrrolo[3,2-d]-pyrimidin-4-one, monohydrochloride, m.p. 195° dec.

(cc) 2-Amino-3,5-dihydro-7-[2-hydroxy-1-(3-pyridinyl)ethyl]-4H-pyrrolo[3,2-d]-pyrimidin-4-one, m.p.>250° C.

(dd) 2-Amino-3,5-dihydro-7-[2-hydroxy-1-(3-thiophenyl)ethyl]-4H-pyrrolo[3,2-d]-pyrimidin-4-one, m.p.>250° C.

EXAMPLE 4

2-Amino-7-[1-(2-fluorophenyl)-2(R)-(tetrahydropyran-2-yloxy)ethyl]-3,5-dihydro-4H-pyrrolo[3,2-d]pyrimidin-4-one (see example 1, 5.0 g, 14.1 mmol) is dissolved in $CH_2Cl_2$ (150 ml) and treated with N,N-dimethylformamide dimethylacetal (50 mL, 376 mmol) The mixture is stirred overnight and then concentrated on a rotovap to give a yellow solid. The solid is dissolved in MeOH (100 ml) and treated with 1 N HCl (50 mL 50 mmol). The reaction is stirred at room temperature for 5 hours and then concentrated on a rotovap to remove MeOH. The remaining aqueous phase is adjusted to pH 7.0 using saturated aqueous $NaHCO_3$. A white solid precipitates, is collected by filtration, and then rinsed with $Et_2O$. Recrystallization (MeOH/water) provides 2-dimethylformamidino-7-[1-(2-fluorophenyl)-2(R)-(tetrahydropyran-2-yloxy)ethyl]-3,5-dihydro-4H-pyrrolo[3,2-d]pyrimidin-4-one as a white solid, m.p. 257–259° C. dec.

The above compound (1.0 g, 3.1 mmol), 2-methyl-2-methoxypropionic acid (0.4 g, 3.4 mmol), dimethylaminopyridine (188 mg, 1.5 mmol) and 1-ethyl-3-(3-dimethylamino-propyl)carbodiimide hydrochloride (1.2 g, 6.1 mmol) are combined and dissolved in $CH_2Cl_2$ (75 ml). The reaction is stirred under an inert atmosphere for 1.5 hours and then transferred to a separatory funnel. The mixture is partitioned between $CH_2Cl_2$ and water (150 ml). The organic phase is separated, washed with brine (75 ml), dried over $MgSO_4$, and then concentrated on a rotovap. Flash chromatography (3–6% $MeOH/CH_2Cl_2$) provides the purified N-protected acylation product. The N-protected acylated derivative (800 mg, 1.9 mmol) is dissolved in EtOH (50 ml) and treated with $NaBH_4$ (200 mg, 5.3 mmol) for 2 hours at room temperature. The EtOH is removed on a rotovap and the residue partitioned between EtOAc (150 ml) and water (150 ml). The organic phase is separated, washed with brine (75 ml), dried over $MgSO_4$ and concentrated on a rotovap. Flash chromatography (3% $MeOH/CH_2Cl_2$) provides 2-amino-7-[1-(2-fluorophenyl)-2-(R)-(2-methyl-2-methoxypropionyloxy)-ethyl]-3,5-dihydro-4H-pyrrolo[3,2-d]pyrimidin-4-one as a white solid, m.p. 150–155° C.

EXAMPLE 5

(a) Methyl 3-amino-4-[1-(2-methoxyphenyl)-2-[(tetrahydropyran-2-yloxy)ethyl]-1H-pyrrole-2-carboxylate (600 mg, 1.6 mmole), isopropanol (10 ml), cyanamide (3 g, 71.4 mmole) and concentrated HCl (0.3 ml) are placed in a thick walled, sealable glass tube. The tube is sealed with a teflon stopper and heated at 120° C. for 8 hours. The system is allowed to cool before being carefully opened, the solvents and other volatile material are removed under reduced pressure. Water (5 ml) and ethyl acetate (5 ml) are added and after 1 hour at room temperature a white precipitate forms. This solid is filtered off and identified (by nmr and TLC) as the desired product. The solid is dissolved in methanol and the solution is filtered. The product is crystallized by the addition of ethyl ether, separated by filtration and dried in an oven at 50° C. under reduced pressure to give 2-amino-3,5-dihydro-7-[2-hydroxy-1-(2-methoxyphenyl)ethyl]-4H-pyrrolo[3,2-d]pyrimidin-4-one of example 3(g), m.p. 262–265° C.

(b) Similarly prepared is 2-amino-3,5-dihydro-7-[2-(R)-hydroxy-1-(2-fluorophenyl)ethyl]-4H-pyrrolo[3,2-d]pyrimidin-4-one of example 1, m.p. 263–264° C.

EXAMPLE 6

A mixture of 69.80 g of crude ethyl 3-amino-4-[1-(2-fluorophenyl)-2(R)-[(triphenylmethoxy)ethyl]-2-1H- pyrrole-2-carboxylate and 300 mL of anhydrous 2B ethyl alcohol (containing 0.5% toluene) is stirred for 20 minutes at 20–25° C. 54 mL of conc. HCl (36.5–38%) is added at 20–40° C. over a period of 15 minutes. The mixture is heated to 40–45° C. (bath temperature: 45–50° C.), stirred at 40–45° C. for 16 hours, cooled to 0–5° C., and filtered. The filter cake is washed with 2×50 mL of 2B ethanol. The filtrate is heated to 40–45° C. (bath temperature: 45–50° C.) and a total of 100 mL of 50% cyanamide (w/w in water) is added in five equal 20-mL portions at 2 hour intervals. The pH is checked after each addition; if the pH is above 2, 5 mL of conc. HCl is added. Two hours after the last addition of cyanamide, the reaction mixture is cooled to 0–5° C. (bath temperature: 0–2° C.), 45 mL of 50% sodium hydroxide is then added to adjust the pH to 12 at a rate to maintain the internal temperature below 15° C. The mixture is cooled to 0–5° C. and stirred at 0–5° C. for 2 hours. Then, 45 mL of conc. HCl (36.5–38.0%) is added to adjust pH to 2 at a rate to maintain the internal temperature at 5–10° C. (bath temperature: 0–5° C.). The mixture is concentrated under reduced pressure (40–50 mbar; bath temperature 45–50° C.) until the residue volume is about 350 mL; 200 mL of water is added and the mixture is stirred at 20–25° C. for 20 minutes. Then 150 mL of ethyl acetate is added and the mixture is again stirred for 20 minutes. The organic layer is separated and the aqueous layer is extracted with 100 mL of ethyl acetate. The combined organic layers are washed with 180 mL of 0.1 N HCl solution in two equal 90-mL portions. All the aqueous layers are combined and cooled to 0–5° C. (bath temperature: –5 to 0° C.; 15 mL 50% of NaOH (w/w) is added to adjust the pH to 8–9 at a rate to maintain the internal temperature at 0–15° C. with vigorous agitation. The mixture is stirred at 0–5° C. for 2 hours, and then at room temperature for 16 hours. The solid is collected by filtration and washed with a total of 200 mL of water in two equal 100-mL portions to afford (after drying at 50° C./20–45 mbar for 16 hours) crude 2-amino-7-[1-(2-fluorophenyl)-2(R)-hydroxyethyl]-3,5-dihydro-4H-pyrrolo[3,2-d]pyrimidin-4-one.

A mixture of 25.69 g of crude 2-amino-7-[1-(2-fluorophenyl)-2(R)-hydroxyethyl]-3,5-dihydro-4H-pyrrolo[3,2-d]pyrimidin-4-one and 98 mL of 1.0 N NaOH is heated to 40–45° C. (bath temperature: 45–50° C.) and stirred for 30 minutes to obtain a clear brown solution. Charcoal (1.29 g) is added, the mixture is stirred at 40–45° C. for 20 minutes and filtered through 3 g of Celite. The filter cake is washed with 20 mL of water. After addition of 120 mL of 2B ethanol the solution is heated to 35–40° C. (bath temperature: 40–45° C.) and treated with 10.2 mL of acetic acid dropwise at 35–45° C. over 20 minutes with moderate agitation to crystallize the product. The mixture is stirred at 40–45° C. (bath temperature: 45–50° C.) for 2 hours, cooled to 20–25° C. (bath temperature: 20–25° C.) over a period of 30 minutes, and is stirred for 4 hours at the same temperature. The solid is collected and washed with a total of 80 mL of 50% aq. 2B ethanol in two equal portions. A suspension of the resulting product in 150 mL of water is stirred for 4 hours. The solid is filtered off, washed with a total of 60 mL of water in two equal portions of 30 mL each, and is dried at 50° C. under reduced pressure (25–40 mbar) for 16 hours to obtain pure 2-amino-7-[1-(2-fluorophenyl)-2(R)-hydroxyethyl]-3,5-dihydro-4H-pyrrolo[3,2-d]pyrimidin-4-one of example 1.

The starting material is prepared as follows:

A solution of 50.0 g of o-fluorophenylacetic acid in 150 mL of toluene and 2.2 g of N,N-dimethylformamide is added to 50.2 g (31.7 mL) of thionyl chloride with efficient stirring over a period of 20 minutes while maintaining an internal temperature of 20–25° C. After addition, the mixture is stirred for 3 hours at 20–25° C., and concentrated to dryness under reduced pressure (66–76 mm Hg, bath temperature 65–70° C.) to obtain 2-fluorobenzenacetyl chloride as an oil.

A solution of 46.0 g of (R)-4-phenyl-2-oxazolidinone in 300 g (338 mL) of peroxide-free tetrahydrofuran is cooled to –5 to 0° C. (bath temperature –10 to –5° C.) over a period of 15 minutes. 145.2 g (166.8 mL) of 25% w/w potassium t-amylate/toluene solution is added over a period of 25 minutes while maintaining an internal temperature below 0° C. The reaction mixture is warmed to 20±5° C. within 1 hour and stirred at this temperature for 2.5–3 hours. The mixture is cooled to –15 to –5° C. over a period of 30 minutes, and crude 2-fluorobenzenacetyl chloride (obtained above) is added over a period of 45 minutes while maintaining an internal temperature below –5° C. (bath temperature –15 to –10° C.). After the addition is completed, the mixture is warmed to 20±5° C. over a period of 1 hour, and diluted with 100 mL of toluene. This is added to 500 mL of saturated citric acid monosodium salt solution (100 g in 450 g of water) and the mixture is stirred for 5 minutes. The organic layer is separated, and washed with 1 L of sodium chloride solution (200 g in 800 g of water) in two equal portions of 500 mL each. The solution is concentrated to dryness under reduced pressure (66–76 mm Hg, bath temperature 65–70° C.) to obtain 3-[2-(2-fluorophenyl)-1-oxoethyl]-4(R)-phenyl-2-oxazolidinone as a semi-solid. The semi-solid is suspended in 450 mL of t-butyl methyl ether and the mixture is heated to reflux (53–58° C.) to obtain a solution; 225 mL of t-butyl methyl ether is then distilled off at atmospheric pressure (bath temperature 60–65° C.). The resulting mixture is cooled to 20–25° C., and stirred at this temperature for 16 hours, then cooled to –5 to 0° C. and stirred at this temperature for additional 2 hours and filtered. The resulting solid is dried under vacuum (66–76 mm Hg) at 45–50° C. for 12 hours to obtain 3-[2-(2-fluorophenyl)-1-oxoethyl]-4(R)-phenyl-2-oxazolidinone as a white crystalline solid. Alternately, 3-[2-(2-fluorophenyl)-1-oxoethyl]-4-(R)-phenyl-2-oxazolidinone is prepared as follows:

A mixture of 107.7 g of o-fluorophenylacetic acid, 100 g of (R)-4-phenyl-2-oxazolidinone, 186 g of triethylamine, and 1.0 L of toluene is heated to an internal temperature of 80° C. (heating mantle temperature 90° C.) to afford a solution; 88.5 g of pivaloyl chloride is added over period of 30 minutes with efficient stirring while maintaining an internal temperature 80–85° C. and stirred at this temperature for 2 hours. An additional 44.1 g of pivaloyl chloride is added over a period of 15 minutes while maintaining an internal temperature 80–85° C., and the mixture is stirred at the same temperature for additional 3 hours. The mixture is cooled to an internal temperature of 40° C. over a period of 10 minutes and 300 mL of water (prewarmed to 40° C.) is added over a period of 2 minutes while maintaining an internal temperature below 40–45° C. (slightly exothermic reaction). The organic layer is separated and washed with 358 mL of 2.17 N HCl solution (prewarmed to 40° C.) and 100 mL of water (prewarmed to 40° C.) sequentially while maintaining an internal temperature 40–45° C. and concentrated to dryness under reduced pressure (58–61 mbar; bath temperature, 51–53° C.) to obtain 3-[2-(2-fluorophenyl)-1-oxoethyl]-4-(R)-phenyl-2-oxazolidinone as a semi-solid. The semi-solid is suspended in 400 mL of tert-butyl methyl ether and the mixture is heated to reflux (internal temperature of 58–61° C.) to obtain a yellow solution. The solution is cooled to 20–25° C. over a period of 20 minutes and stirred at this temperture for 4 hours. The mixture is then further cooled to 5 to 9° C. and stirred at this temperature for additional 2 hours. The solids are collected by filtration and washed with a total of 27 mL of tert-butyl methyl ether (precooled to 5–9° C.) in three equal portions of 9 mL each. The product is dried at 45–50° C. (86–99 mbar) for 12 hours to obtain optically pure of 3-[2-(2-fluorophenyl)-1-oxoethyl]-4-(R)-phenyl-2-oxazolidinone as a white solid; m.p. 110–111° C.; $[\alpha]_D$: –110.4 (c=1, MeOH)

A solution of 546 g of 3-[2-(2-fluorophenyl)-1-oxoethyl]-4-(R)-phenyl-2-oxazolidinone in 2,180 mL of peroxide-free tetrahydrofuran is cooled to an internal temperature of –5 to –8° C. A solution of 1,773 mL of lithium hexamethyldisilazide in tetrahydrofuran (1M) is added over a period of 55 minutes, while maintaining an internal temperature of 0 to –5° C. The solution is stirred at an internal temperature of 0 to –5° C. for 1 hour and then cooled to an internal temperature of –20° C. 150 mL of Bromoacetonitrile is added over a period of 40 minutes, while maintaining an internal temperature of –15 to –20° C. The reaction mixture is stirred at an internal temperature of –15 to –20° C. for 4.5 hours and added to a solution of 478 g of NaCl in 2,164 mL of water and 214 g of concentrated HCl cooled to an internal temperature of 0 to 5° C., over a period of 20 minutes, while maintaining the internal temperature below 9° C. After addition of 500 mL of tetrahydrofuran, the slurry is stirred for 15 minutes at an internal temperature of 5 to 8° C., and then warmed to room temperature (17 to 19° C.) over a period of 30 minutes. The organic layer is separated and washed with a solution of 632 g of NaCl in 2,180 mL of water. The slurry is stirred for 15 minutes, the organic layer is separated and concentrated under reduced pressure (20 mm Hg; bath temperature 45° C.) to a final volume of 1.4–1.6L. 2,500 mL of t-Butyl methyl ether is added and the slurry is vigorously stirred for 1 hour at room temperature (18 to 20° C.). The solid is collected and washed with 2×150 mL of t-butyl methyl ether and dried at 45 to 50° C. (20 mm Hg) for 20 hours to obtain β-(R)-(2-fluorophenyl)-γ,2-dioxo-4(R)-phenyl-3-oxazolidinebutyronitrile as an off-white crystalline solid.

A mixture of 33.8 g of β-(R)-(2-fluorophenyl)-γ,2-dioxo-4(R)-phenyl-3-oxazolidinebutyronitrile, 507 mL of peroxide-free tetrahydrofuran and 2.1 1 g of water is stirred and cooled to 0 to –3° C. (bath temperature –8 to –10° C.) to afford a white slurry. A solution of 75 mL of 2 M solution of lithium borohydride in tetrahydrofuran is added over a period of 15 minutes while maintaining an internal temperature of –0° C. (bath temperature –10 to –5° C.). The mixture is stirred at 0° C. for an additional 1 hour and 125 mL of 2 N hydrochloric acid is added over a period of 30 minutes while maintaining an internal temperature of 0to 3° C. 110 mL of saturated sodium chloride solution is added and the mixture is warmed to 15–18° C. over a period of 10 minutes. The top organic layer is separated and the aqueous layer is extracted with 100 mL of toluene. The organic layers are combined and washed with 100 mL of saturated sodium chloride solution. The organic solution then is filtered and concentrated under reduced pressure (50–100 mbar; bath temperature 45–50° C.) to 150 mL volume. To the residue is added 100 mL of toluene and the mixture is concentrated under reduced pressure (50–100 mbar; bath temperature 45–50° C.) to 75–85 mL volume. The mixture is cooled to 0° C. (bath temperature –3 to 0° C.) and stirred for 1 to 2 hours. The resulting solid is collected and washed with 45 mL of toluene (precooled to 5° C.) in three equal portions of 15 mL each. The filtrate is concentrated to dryness under reduced pressure (30–100 mbar; bath temperature 45–50° C.) to obtain crude 2-fluoro-(β-(R)-hydroxymethyl)benzenepropionitrile as an oil, optical purity: 95% ee (by chiral HPLC).

Alternately, 2-fluoro-(β-(R)-hydroxymethyl)benzenepropionitrile can be prepared as follows:

To a slurry of 60.0 g of β-(R)-(2-fluorophenyl)-γ,2-dioxo-4(R)-phenyl-3-oxazolidinebutyronitrile in 540 mL of peroxide-free tetrahydrofuran is added a freshly preformed solution of 27.0 g of $NaBH_4$ in 170 mL of water over a period of 45 minutes while maintaining an internal temperature 20 to 25° C. (bath temperature: 18 to 20° C.). The reaction mixture is stirred at 20–25° C. for 1 hour. A solution of 40 g of NaCl in 400 mL of 2 N hydrochloric acid is added over a period of 45 minutes, while maintaining an internal temperature of 20 to 25° C. (bath temperature: 15 to 20° C.). This addition is exothermic and causes vigorous hydrogen gas evolution. The top organic layer is separated and the aqueous layer is extracted with 175 mL of toluene. The combined organic layers are washed with 175 mL of saturated sodium chloride solution, filtered and concentrated to dryness under reduced pressure (50–100 mbar, bath temperature 45–50° C.). To the residue is added 100 mL of toluene, and the mixture is concentrated under reduced pressure (50–100 mbar; bath temperature 45–50° C.) to a volume of about 110 mL. The mixture is cooled to 0 to 5° C. and stirred for 1–2 hours. The solids are filtered off and washed with a total of 75 mL of cold (~5° C.) toluene in three equal portions of 25 mL each. The filtrate is concentrated to dryness under reduced pressure (30–100 mbar; bath temperature 45–50° C.) to obtain optically pure crude 2-fluoro-(β-(R)-hydroxymethyl)benzenepropionitrile as an oil which is stored below 0° C. and used for the next step as is.

A mixture of 64.5 g of 2-fluoro-β(R)-(hydroxymethyl)benzenepropionitrile, 450 mL of toluene, and 106.2 g of triphenylmethyl chloride is stirred at 20–22° C. for 10 minutes to afford a brown solution; 54 g of triethylanine is added rapidly over a period of 10 minutes while maintaining an internal temperature of <30° C. The reaction mixture is stirred at an internal temperature of 35° C., (external temperature: 41° C.) for 24 hours to obtain a light, brown suspension. The tritylation reaction is catalyzed by water. The reaction progress is monitored by HPLC to determine if water addition is required. If after 4 hours, more than about 30% of starting material is left, 1 g of water is added. If after 20 hours, the amount of starting material is still more than 15%, an additional 1 g of water is added. After 24 hours, an additional 17 g of triphenylmethyl chloride and 7 g of triethylamine are added, the resulting suspension is stirred for an additional 24 hours at 35° C. and cooled to room temperature; 58 mL of methanol is added dropwise over 10 minutes, while maintaining an internal temperature of 30–35° C. The reaction mixture is stirred for 40 minutes at an internal temperature of 20–25° C. The mixture is concentrated under reduced pressure (20–50 mbar; bath temperature 45–50° C.) to obtain crude 2-fluoro-β(R)-[(triphenylmethyl)oxy]benzenepropionitrile as a red semi-solid. The semi-solid is suspended in 800 mL of methanol. The slurry is stirred at an internal temperature of 50° C. for 40 minutes, then at 20–22° C. for 30 minutes, and filtered to obtain, after washing the product with methanol and drying it under vacuum (30 mbar) at 45–50° C. for 4 hours or to constant weight, 2-fluoro-β(R)-[(triphenylmethyl)oxy]benzenepropionitrile; chiral purity: >99% ee.

A mixture of 59.81 g of 2-fluoro-β(R)-[(triphenylmethyl)oxy]benzenepropionitrile and 300 mL of anhydrous peroxide-free tetrahydrofuran is stirred at 20–25° C. under nitrogen for 15 minutes. The yellowish solution is cooled –10° C. (internal temperature, bath temperature: –15° C.). A solution of 78 mL of 2.0 M lithium diisopropylamide in heptane/THF is added through an addition funnel over a period of 20 minutes while maintaining an internal temperature −10 to −5° C. The mixture is stirred at −10 to −5° C. for 15 minutes, and 29 mL of ethyl formate is added over a period of 20 minutes while maintaining an internal temperature −10 to −5° C. The reaction mixture is stirred at −10 to −5° C. for 30 minutes and added to a solution of 15 mL of glacial acetic acid and 300 mL of 20% sodium chloride solution over a period of 20 minutes while maintaining an internal temperature 0 to 5° C. After stirring the mixture at 0 to 5° C. for 15 minutes, the organic layer is separated and the aqueous layer is extracted with 150 mL of ethyl acetate. The organic layers are combined and washed with 300 mL saturated sodium bicarbonate solution (the pH of the aqueous layer should be 8–10), and then with 300 mL saturated sodium chloride solution. The organic solution is dried and concentrated to dryness under reduced pressure (20–50 mbar; bath temperature 40–45° C.) to obtain crude 2-fluoro-α-(hydroxymethylidenyl)-β-(R)-[(triphenylmethoxy)methyl]benzenepropionitrile as an oil. The product is unstable and should be stored at 0 to 4° C. until used in the next step.

A mixture of 34.92 g of sodium acetate, 60.05 g of diethyl aminomalonate hydrochloride, and 150 mL of anhydrous 2B ethyl alcohol (containing 0.5% of toluene) is stirred at 20 to 25° C. for 20 minutes. A solution of 98 g of crude 2-fluoro-α-(hydroxymethylidenyl)-β-(R)-[(triphenylmethoxy)methyl]benzenepropionitrile in 150 mL of anhydrous 2B ethyl alcohol is added at 20 to 25° C. over a period of 20 minutes. The mixture is stirred at 20 to 25° C. for 3 days. Then 240 mL of ethyl acetate and 300 mL of water are added and the mixture is stirred at 20 to 25° C. for 20 minutes. The organic layer is separated and the aqueous layer is extracted with 120 mL of ethyl acetate. The organic layers are combined, washed first with then 240 mL of saturated sodium bicarbonate solution and 240 mL of saturated sodium chloride solution, and concentrated to dryness under reduced pressure (20–50 mbar; bath temperature 40–45° C.). Toluene (150 mL) is then added, the mixture is stirred at 20 to 25° C. for 20 minutes and concentrated to dryness under reduced pressure (20–50 mbar; bath temperature 40–45° C.). The above process is repeated two additional times with a total of 300 mL of toluene in two equal portions of 150 mL each to obtain crude 2-fluoro-α-[[[di-(ethoxycarbonyl)-methyl]amino]-methylidenyl]-β(R)-[(triphenylmethyloxy)methyl]benzenepropionitrile as an oil.

A mixture of 119.5 g of crude 2-fluoro-α-[[[di-(ethoxycarbonyl)-methyl]amino]-methylidenyl]-β(R)-[(triphenylmethyloxy)methyl]benzenepropionitrile, and 240 mL of anhydrous 2B ethyl alcohol is stirred for 20 minutes and cooled to 10±5° C. (bath temperature: 5° C.). A solution 80 mL of a solution of 21% sodium ethoxide in ethanol is added over a period of 20 minutes while maintaining an internal temperature at 10 to 20° C., and the mixture is stirred at 20 to 25° C. overnight. The reaction mixture is cooled to −5 to 0° C. and 20 mL of acetic acid is added at −5 to 0° C. over a period of 15 minutes. After stirring the mixture for 20 minutes, 300 mL of ethyl acetate and 400 mL of 20% NaCl are added (pH of the aqueous layer should be 4–6), and the mixture is stirred for 20 minutes at same temperature. The organic layer is separated and the aqueous layer is extracted with 120 mL of ethyl acetate. The combined organic layers are washed first with 300 mL of saturated sodium bicarbonate, and then with 300 mL of saturated sodium chloride, filtered and concentrated to dryness under reduced pressure (40–50 mbar; bath temperature 40–45° C.); 150 mL of anhydrous 3A ethyl alcohol (containing 5% isopropanol & 5% MeOH) is added, the mixture is stirred for 20 minutes. The mixture is concentrated to dryness under reduced pressure (40–50 mbar; bath temperature 40–45° C.). The above process is repeated two additional times with a total of 300 mL of anhydrous 3A ethanol. The residue is then dissolved in 180 mL of anhydrous 3A ethyl alcohol. The solution is added to 600 mL of water (precooled to 0 to 5° C.) over a period of 30 minutes while maintaining an internal temperature at 0 to 5° C. (bath temperature: 0±3° C.). The mixture is stirred for 1 hour at 5±5° C. and 200 mL of saturated NaCl solution is added. Stirring is continued for 1 hour at 5±5° C., the solid is collected by filtration, washed with 2×100 mL of water, and dried under vacuum (30 mbar) at room temperature (22–25° C.) for two days to obtain crude ethyl 3-amino-4-[1-(2-fluorophenyl)-2(R)-[(triphenylmethoxy)ethyl-2-1H-pyrrole-2-carboxylate as a brown powder. If a filterable solid is not obtained, the product is extracted with 300 mL of ethyl acetate. The ethyl acetate extract is washed with 200 mL of saturated NaCl, and concentrated to dryness under reduced pressure (40–50 mbar; bath temperature: 45–50° C.). The residue is then dissolved in 300 mL of 3A ethanol and the solution is concentrated to dryness under reduced pressure (40–50 mbar; bath temperature: 45–50° C.) to yield the crude intermediate which can be used directly in the next step.

EXAMPLE 7

Preparation of 1,000 capsules each containing 25 mg of the active ingredient, using the following ingredients:

| Active ingredient | 25.00 g |
|---|---|
| Lactose | 192.00 g |
| Modified starch | 80.00 g |
| Magnesium stearate | 3.00 g |

Procedure: All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 30 mg of said mixture each, using a capsule filling machine.

What is claimed is:

1. A process for the preparation of a compound of the formula

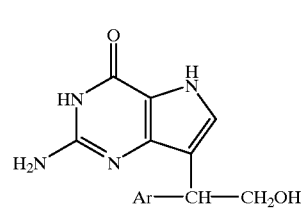

(I)

or a tautomer thereof, wherein Ar represents biaryl, carbocyclic or heterocyclic aryl, or of a pharmaceutically acceptable salt thereof, as a substantially pure enantiomer thereof which comprises:

(a) condensing a compound of the formula

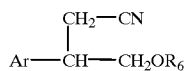
(XIX)

as a substantially pure enantiomer, wherein Ar has meaning as defined above and $R_6$ is an O-protecting group with a lower alkyl ester of formic acid to obtain a compound of the formula

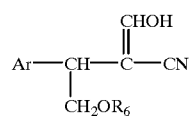
(XX)

as a substantially pure enantiomer;

(b) then condensing the compound so obtained with a compound of the formula

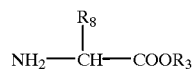
(XXI)

wherein $R_8$ is hydrogen or $COOR_3$ and $R_3$ is lower alkyl, to obtain a compound of the formula

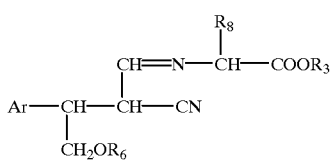
(XXII)

or an enamine tautomer thereof, as a substantially pure enantiomer;

(c) then cyclizing the compound so obtained to a compound of the formula

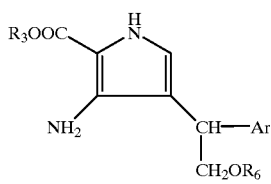
(XXIII)

as a substantially pure enantiomer;

(d) and then condensing the compound so obtained
  (1) with a carbocyclic aroyl isothiocyanate and treatment of the product so obtained with an alkyl halide followed by anhydrous ammonia; or
  (2) with cyanamide in acid, optionally followed by treatment with a base;

and wherein in the above definitions, carbocyclic and heterocyclic aryl are either monocyclic or bicyclic; monocyclic carbocyclic aryl represents phenyl or phenyl substituted by one to three substituents, such being lower alkyl, hydroxy, lower alkoxy, acyloxy, halogen, cyano, trifluoromethyl, carbocyclic aryloxy or carbocyclic aryl-lower alkoxy; bicyclic carbocyclic aryl represents 1- or 2-naphthyl or 1- or 2-naphthyl substituted by lower alkyl, lower alkoxy or halogen; monocyclic heterocyclic aryl represents thienyl, furanyl, pyridyl, pyrrolyl, thiazolyl, pyrazinyl, pyridazinyl or pyrazolyl, or thienyl, furanyl or thiazolyl substituted by lower alkyl, or pyridyl substituted by lower alkyl, halogen or cyano; bicyclic heterocyclic aryl represents indolyl or benzothiazolyl, or indolyl or benzothiazolyl substituted by hydroxy, lower alkyl, lower alkoxy or halogen; and biaryl represents phenyl substituted by carbocyclic aryl or heterocyclic aryl located ortho, meta or para to the point of attachment of the phenyl ring; and acyloxy is lower alkanoyloxy, lower alkoxycarbonyloxy, monocyclic carbocyclic aroyloxy or monocyclic heterocyclic aroyloxy.

2. A process according to claim 1 for the preparation of a compound having the configuration of the formula

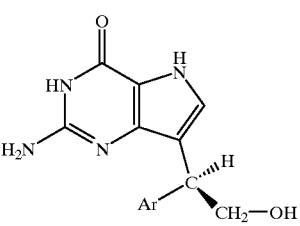
(Ia)

or a tautomer thereof, wherein Ar represents biaryl, carbocyclic or heterocyclic aryl; or of a pharmaceutically acceptable salt thereof.

3. A process for the preparation of a compound of the formula

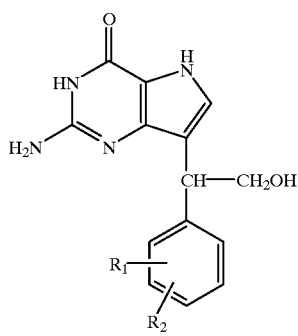

as a substantially pure enantiomer thereof, or a tautomer thereof, wherein $R_1$ and $R_2$ represent independently hydrogen, halo, lower alkyl, hydroxy, lower alkoxy, aryl-lower alkoxy, acyloxy, aryloxy, trifluoromethyl, cyano, (hydroxy, lower alkoxy or acyloxy)-lower alkyl, or (lower alkylthio, lower alkylsulfinyl or lower alkylsulfonyl)-lower alkyl; or $R_1$ and $R_2$ together on adjacent carbon atoms represent lower alkylenedioxy; or of a pharmaceutically acceptable salt thereof; which comprises:

(a) condensing a compound of the formula

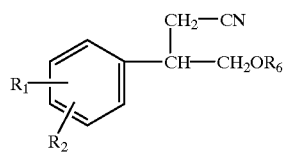

as a substantially pure enantiomer, wherein $R_1$ and $R_2$ have meaning as defined above and $R_6$ is an O-protecting group, with a lower alkyl ester of formic acid to obtain a compound of the formula

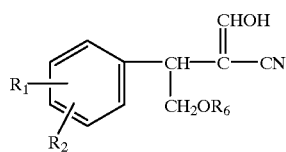

as a substantially pure enantiomer;

(b) then condensing the compound so obtained with a compound of the formula

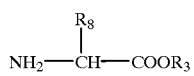

wherein $R_8$ is hydrogen or $COOR_3$ and $R_3$ is lower alkyl, to obtain a compound of the formula

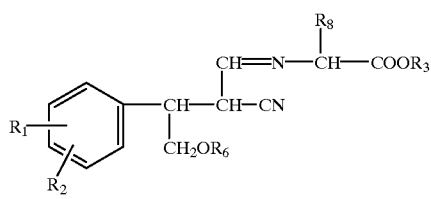

or an enamine tautomer thereof, as a substantially pure enantiomer;

(c) then cyclizing the compound so obtained to a compound of the formula

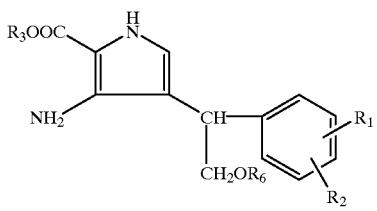

as a substantially pure enantiomer;

(d) and then condensing the compound so obtained
  (1) with a carbocyclic aroyl isothiocyanate and treatment of the product so obtained with an alkyl halide followed by anhydrous ammonia; or
  (2) with cyanamide in acid, optionally followed by treatment with a base;

and wherein in the above definitions aryl is carbocyclic or heterocyclic aryl; carbocyclic and heterocyclic aryl are either monocyclic or bicyclic; monocyclic carbocyclic aryl represents phenyl or phenyl substituted by one to three substituents, such being lower alkyl, hydroxy, lower alkoxy, acyloxy. halogen, cyano, trifluoromethyl, carbocyclic aryloxy or carbocyclic aryl-lower alkoxy; bicyclic carbocyclic aryl represents 1- or 2-naphthyl or 1- or 2-naphthyl substituted by lower alkyl, lower alkoxy or halogen; monocyclic heterocyclic aryl represents thienyl, furanyl, pyridyl, pyrrolyl, thiazolyl, pyrazinyl, pyridazinyl or pyrazolyl, or thienyl, furanyl or thiazolyl substituted by lower alkyl, or pyridyl substituted by lower alkyl, halogen or cyano; bicyclic heterocyclic aryl represents indolyl or benzothiazolyl, or indolyl or benzothiazolyl substituted by hydroxy, lower alkyl, lower alkoxy or halogen; and acyloxy is lower alkanoyloxy, lower alkoxycarbonyloxy, monocyclic carbocyclic aroyloxy or monocyclic heterocyclic aroyloxy.

4. A process according to claim 3 of a compound being the enantiomer of the formula

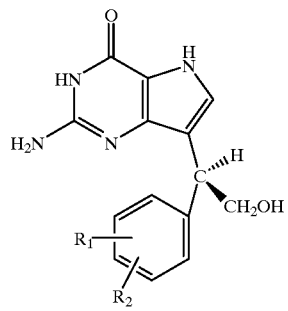

(IIa)

or a tautomer thereof, wherein $R_1$ and $R_2$ represent independently hydrogen, halo, lower alkyl, hydroxy, lower alkoxy, aryl-lower alkoxy, acyloxy, aryloxy, trifluoromethyl, cyano, (hydroxy, lower alkoxy or acyloxy)-lower alkyl, or (lower alkylthio, lower alkylsulfonyl or lower alkylsulfonyl)-lower alkyl; or $R_1$ and $R_2$ together on adjacent carbon atoms represent lower alkylenedioxy; or of a pharmaceutically acceptable salt thereof.

5. A process according to claim 1 wherein Ar is thienyl, furanyl, pyridyl, pyrrolyl, thiazolyl, pyrazinyl, pyridazinyl or pyrazolyl.

6. A process according to claim 2 wherein Ar thienyl, furanyl, pyridyl, pyrrolyl, thiazolyl, pyrazinyl, pyridazinyl or pyrazolyl.

7. A process according to claim 1 wherein Ar is phenyl, halophenyl or pyridyl.

8. A process according to claim 2 wherein Ar is phenyl, halophenyl or pyridyl.

9. A process according to claim 1 wherein Ar is phenyl, chlorophenyl or fluorophenyl.

10. A process according to claim 2 wherein Ar is phenyl, chlorophenyl or fluorophenyl.

11. A process according to claim 1 wherein Ar is phenyl or o-fluorophenyl.

12. A process according to claim 2 wherein Ar is phenyl or o-fluorophenyl.

13. A process according to claim 2 wherein Ar is phenyl.

14. A process according to claim 2 wherein Ar is o-fluorophenyl.

* * * * *

UNITED STATES PATENT AND TRADEMARK OFFICE
CERTIFICATE OF CORRECTION

PATENT NO. : 6,043,365
DATED : March 28, 2000
INVENTOR(S) : Mcquire et al.

It is certified that error appears in the above-identified patent and that said Letters Patent is hereby corrected as shown below:

<u>Column 30,</u>
First line of the said claim should read:
-- A process according to claim 2 wherein Ar is thienyl, --.

Signed and Sealed this

Seventh Day of January, 2003

JAMES E. ROGAN
*Director of the United States Patent and Trademark Office*